US008622917B2

(12) United States Patent
Eto et al.

(10) Patent No.: US 8,622,917 B2
(45) Date of Patent: Jan. 7, 2014

(54) ELECTRONIC SPHYGMOMANOMETER

(75) Inventors: Mika Eto, Takatsuki (JP); Yukiya Sawanoi, Nara (JP)

(73) Assignee: Omron Healthcare Co., Ltd., Kyoto (JP)

( * ) Notice: Subject to any disclaimer, the term of this patent is extended or adjusted under 35 U.S.C. 154(b) by 280 days.

(21) Appl. No.: 13/161,004

(22) Filed: Jun. 15, 2011

(65) Prior Publication Data

US 2011/0251499 A1 Oct. 13, 2011

Related U.S. Application Data

(63) Continuation of application No. PCT/JP2009/070542, filed on Dec. 8, 2009.

(30) Foreign Application Priority Data

Dec. 18, 2008 (JP) ................................. 2008-322799

(51) Int. Cl.
*A61B 5/02* (2006.01)
(52) U.S. Cl.
USPC .......................................... 600/490; 600/485
(58) Field of Classification Search
USPC .................................................. 600/484–525
See application file for complete search history.

(56) References Cited

FOREIGN PATENT DOCUMENTS

| EP | 1967133 | * | 11/2006 |
|---|---|---|---|
| EP | 1967133 A1 | | 9/2008 |
| JP | 05-329113 | * | 12/1993 |
| JP | 5-329113 A | | 12/1993 |
| WO | 2007/072647 A1 | | 6/2007 |
| WO | 2010/071052 A1 | | 6/2010 |

OTHER PUBLICATIONS

Patent Abstract for Japanese Publication No. 05-329113 Published Dec. 14, 1993 (1 page).
Notification of Reciept of Record Copy for International Application No. PCT/JP2009/070542 mailed Jan. 22, 2010 (2 pages).
Notification Concerning Submission or Transmittal of Priority Document for International Application No. PCT/JP2009/070542 mailed Jan. 27, 2010 (6 pages).
First Notice Informing the Applicant of the Communication of the International Application (to Designated Offices Which Do Not Apply the 30 Month Time Limit Under Article 22(1)) for International Application No. PCT/JP2009/070542 mailed Jul. 22, 2010 (1 page).

* cited by examiner

*Primary Examiner* — Michael Kahelin
*Assistant Examiner* — Mitchell Alter
(74) *Attorney, Agent, or Firm* — Osha Liang LLP

(57) ABSTRACT

An electronic sphygmomanometer has a causing unit that causes a constant volume change in a cuff and a causing processing unit for controlling a drive of the causing unit for a period for which a first pressure control (for example, depressurization control) is made so as to execute a process for giving a constant volume change to the cuff. Further, the electronic sphygmomanometer includes a measurement control unit that controls based on a cuff pressure signal measurement of a pulse wave amplitude and a pressure change property with respect to the volume change. The electronic sphygmomanometer includes a correction processing unit that corrects the measured pulse wave amplitude based on the measured pressure change property and a blood pressure calculating unit that calculates a blood pressure value based on the corrected pulse wave amplitude.

7 Claims, 16 Drawing Sheets

ELECTRONIC SPHYGMOMANOMETER

BACKGROUND OF THE INVENTION

1. Technical Field

The present invention relates to an electronic sphygmomanometer, and particularly relates to the electronic sphygmomanometer that detects a volume change of a blood vessel as a pressure change of a cuff, namely, an amplitude of a pressure pulse wave, and calculates a blood pressure value using the detected amplitude of the pressure pulse wave.

2. Background Art

Electronic sphygmomanometers for measuring a blood pressure using an amplitude of a pressure pulse wave (hereinafter, "a pulse wave amplitude") like in an oscillometric method have been conventionally present. The oscillometric method is a method for pressurizing or depressurizing a cuff wrapped around a part of an organism to acquire a volume change of the cuff obtained from a volume change of a pressurized blood vessel as a pressure change of the cuff, namely, the pulse wave amplitude and calculating a blood pressure.

In such electronic sphygmomanometers, it is found that because a pressure and a volume of a cuff are not in proportional to each other due to a cuff property, detection accuracy of a volume change in a blood vessel varies according to an arm circumference and pressures of a cuff. That is to say, even if the same blood pressure values are obtained, an error is caused in a level of the pulse wave amplitude due to factors such as differences in the cuff pressure and the arm circumference. For this reason, such factors are error factors of the blood pressure value.

The following method has been conventionally proposed for preparing a volume change property.

For example, Japanese Unexamined Patent Publication No. 5-329113 (Patent Document 1) describes a method for preparing a volume change property of a cuff with respect to a cuff pressure in advance and converting a signal of the pressure change of the cuff into a volume change so as to measure a blood pressure value using the volume change.

PRIOR ART DOCUMENT

Patent Document

Patent Document 1: Japanese Unexamined Patent Publication No. 5-329113

SUMMARY OF THE INVENTION

In the above method, a pressure of a cuff and a volume change property need to be acquired in advance. However, the volume change property changes infinitely according to a wrapping state of the cuff, an arm circumference and body flexibility. Further, volume change properties of a pump, a valve and a cuff vary also according to temperature, humidity or a secular change. For this reason, in the method where the volume change property is acquired in advance, it is difficult to properly convert a signal of a cuff pressure change into a volume change.

Embodiments of the present invention provide an electronic sphygmomanometer that can accurately calculate a blood pressure value even if a wrapping state of a cuff and an arm circumference vary.

An electronic sphygmomanometer according to one or more embodiments of the present invention includes: a cuff to be wrapped around a measurement site; a pressure adjustment unit for adjusting a pressure in the cuff; a pressure sensor for detecting a cuff pressure signal representing the pressure in the cuff; a causing unit for causing a constant volume change in the cuff; a first pressure control unit for controlling drive of the pressure adjustment unit so as to make a first pressure control for changing the pressure in the cuff to a specified direction; a causing processing unit for controlling drive of the causing unit for a period for which the first pressure control is made and executing a process for causing the constant volume change in the cuff; a measurement control unit for making controls so as to measure a pressure change property with respect to the volume change based on the cuff pressure signal acquired at the time of executing a process of the causing processing unit and measure the pulse wave amplitude based on the cuff pressure signal; a correction processing unit for correcting the measured pulse wave amplitude based on the measured pressure change property; and a blood pressure calculating unit for calculating a blood pressure value based on the corrected pulse wave amplitude.

According to one or more embodiments of the present invention, the causing processing unit causes the volume change successively at a cycle different from that of a heart rate of a person to be measured during a period of the first pressure control, and the measurement control unit includes an acquiring unit for acquiring the cuff pressure signal in chronological order during the period of the first pressure control, and a separation unit for executing a filter process on the acquired cuff pressure signal so as to separate the acquired cuff pressure signal into the pulse wave amplitude and the pressure change property.

According to one or more embodiments of the present invention, the first pressure control is a depressurization control, and the heart rate is calculated based on the cuff pressure signal during pressurization control before transition to the depressurization control.

According to one or more embodiments of the present invention, the causing processing unit causes the volume change at a constant interval during the period of the first pressure control, and the measurement control unit includes a first measurement processing unit for measuring the pressure change property based on the cuff pressure signal output at a specified segment where the volume change is given to the cuff, and a second measurement processing unit for measuring the pulse wave amplitude based on the cuff pressure signal output during the period of the first pressure control and at a segment other than the specified segment.

According to one or more embodiments of the present invention, when the pressure in a cuff has the same pressure value, the first pressure control unit makes the first pressure control in stages in order to measure an amplitude value of the cuff pressure signal at times when the volume change is caused and is not caused.

According to one or more embodiments of the present invention, the causing processing unit causes the volume change at a segment from a maximum point of the cuff pressure signal to a next rising point.

According to one or more embodiments of the present disclosure, the cuff includes a fluid bladder for blood pressure measurement, and a blood flow blocking unit arranged on an upper-stream side with respect to the fluid bladder. A second pressure control unit for making a second pressure control in order to change the pressure in the cuff to a direction opposite to the specified direction, and a blood flow block processing unit for blocking a blood flow of the measurement site using the blood flow blocking unit only for the period of the first pressure control are further provided. The causing processing unit causes the volume change sequentially during the period of the first pressure control. The measurement control unit includes a first measurement processing unit for measuring the pressure change property based on the cuff pressure signal output during the period of the first pressure control, and a second measurement processing unit for measuring the pulse wave amplitude based on the cuff pressure signal output during the period of the second pressure control.

According to one or more embodiments of the present invention, the blood flow blocking unit is a fluid bladder for blocking the blood flow.

According to one or more embodiments of the present invention, the causing unit includes a cylinder and a drive unit for driving the cylinder.

Accordingly to one or more embodiments of the present invention, the drive unit includes a stepping motor.

According to the present invention, a pressure change property is measured, and the pulse wave amplitude is corrected based on the measured pressure change property. Therefore, a blood pressure value can be accurately calculated regardless of a wrapping state of the cuff and an arm circumference.

DETAILED DESCRIPTION

Figure 1:
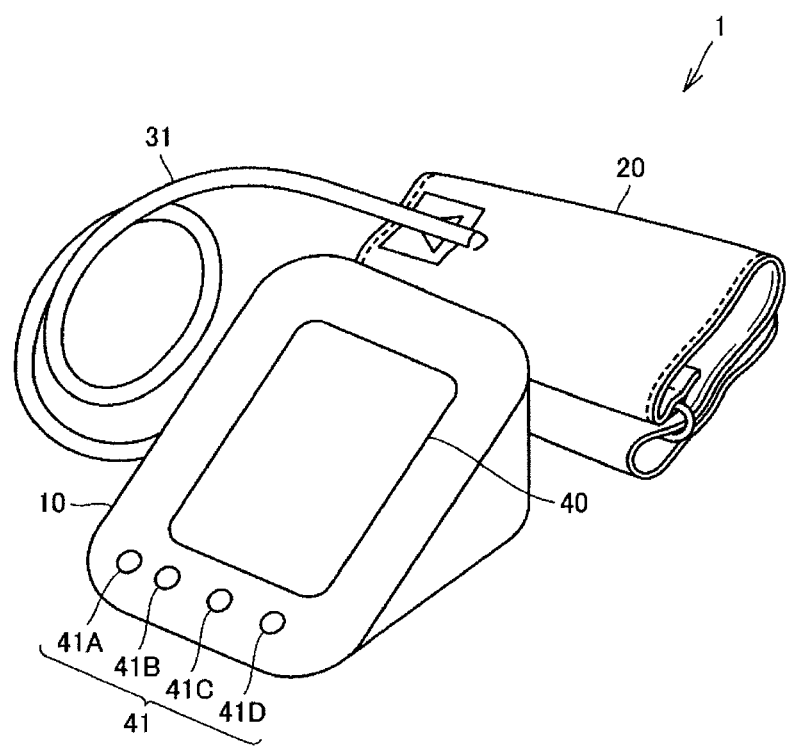
FIG. 1 is an external perspective view illustrating an electronic sphygmomanometer according to one or more embodiments of the present invention.

One or more embodiments of the present invention will be described in detail with reference to the drawings. The same reference numerals are denoted to the same or corresponding portions in the figures, and the description thereof will not be repeated. Further, in embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

First Example

With Regard to Appearance

At first, an appearance of an electronic sphygmomanometer (hereinafter, "a sphygmomanometer") according to one or more embodiments of the present invention will be described below.

FIG. 1 is an external perspective view illustrating a sphygmomanometer 1 according to one or more embodiments of the present invention. The sphygmomanometer 1 calculates a blood pressure value in a manner that a predetermined algorithm is applied to a pulse wave amplitude (an amplitude of a pressure pulse wave) similarly to the oscillometric method.

With reference to FIG. 1, the sphygmomanometer 1 has a main body portion 10, a cuff 20 that can be wrapped around a predetermined measurement site of a person to be measured (for example, an upper arm), and an air tube 31 for connecting the main body portion 10 and cuff 20. A display unit 40 formed by liquid crystal, for example, and an operation unit 41 for accepting instructions from a user (typically the person to be measured) are arranged on a surface of the main body portion 10.

The operation unit 41 has, for example, a power switch 41A for accepting inputs of instructions for powering ON/OFF, a measurement switch 41B for accepting an instruction for starting a measurement, a setting switch 41C for accepting instructions relating to various setting processes, and a memory switch 41D for accepting instructions for reading and displaying past stored values. The operation unit 41 may further has an ID switch (not shown) that is operated in order to input ID (identification) information for identifying a person to be measured.

A summary of one or more embodiments of the present invention will be described herein.

When a blood pressure is measured based on a pulse wave amplitude like the oscillometric method, it is necessary to eliminate error factors caused by not only differences in the cuff pressure but also differences in a wrapping state of the cuff (tight/loose), an arm circumference, and body flexibility in order to accurately calculate a blood pressure value.

Therefore, in accordance with one or more embodiments of the present invention, a constant volume change is caused at every time of measurement (during pressurization or depressurization), the pulse wave amplitude due to a change in an internal pressure of a blood vessel and a property of a pressure change with respect to the constant volume change (hereinafter, "a pressure change property") are measured. As a result, the pressure change property can be acquired according to various measurement conditions (for example, an arm circumference and the wrapping state of the cuff) to be the error factors at every measurement. This will be described concretely with reference to FIG. 2 and FIG. 3.

Figure 2B:
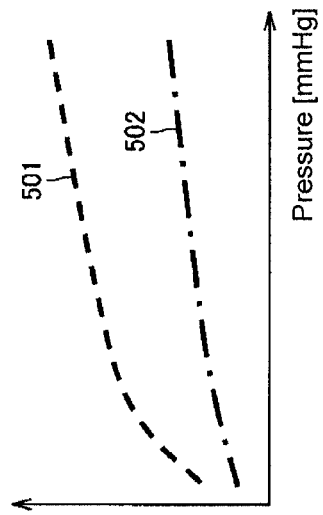
FIGS. 2(A) and 2(B) are diagrams illustrating typical examples of a pressure change with respect to a constant volume change caused by a difference in a circumference of a measurement site.
Figure 2A:
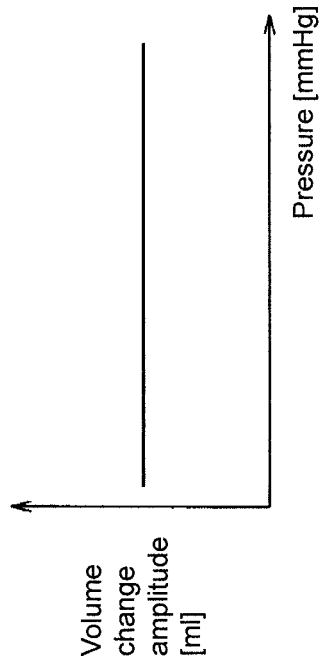

FIGS. 2(A) and 2(B) are diagrams illustrating typical examples of the pressure change property with respect to the constant volume change caused by a difference in a circumference of the measurement site. As shown in FIG. 2(A), the constant volume change is given to the cuff during pressurization or depressurization. FIG. 2(B) illustrates a difference in the pressure change property due to the difference in the circumference of the measurement site when the constant volume change is given to the cuff. The pressure change amplitude in a pressure change property 501 at the time when the measurement site is thinner than a standard size is comparatively larger than that of a pressure change property 502 at the time when the measurement site is thicker than the standard size. Both of them have different change rates.

Figure 3B:
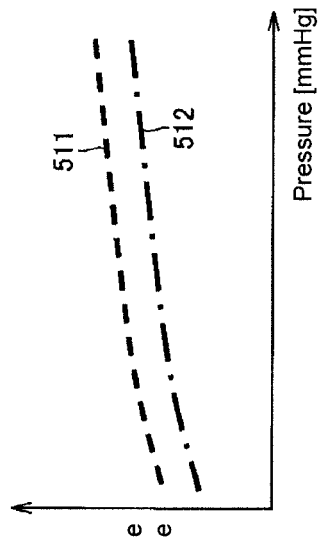
FIGS. 3(A) and 3(B) are diagrams illustrating typical examples of the pressure change with respect to the constant volume change caused by a difference in a wrapping state of a cuff.
Figure 3A:
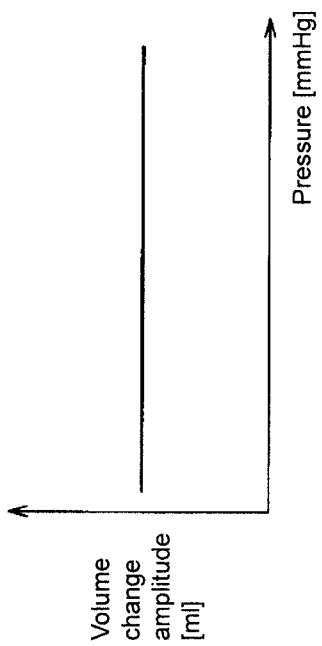

FIGS. 3(A) and 3(B) are diagrams illustrating typical examples of the pressure change property with respect to the constant volume change due to the difference in the wrapping state of the cuff. As shown in FIG. 3(A), the constant volume change is given to the cuff during pressurization or depressurization. FIG. 3(B) illustrates the difference in the pressure change property due to the difference in the wrapping state of the cuff when the constant volume change is given to the cuff. The pressure change amplitude in a pressure change property 511 at the time when the cuff is wrapped tightly around the measurement site is comparatively larger than that in a pressure change property 512 at the time when the cuff is wrapped loosely around the measurement site.

In accordance with one or more embodiments of the present invention, the constant volume change is caused in the cuff at every time of measurement (during pressurization or depressurization), and the pulse wave amplitude caused by the volume change in a blood vessel and the pressure change property with respect to the constant volume change are measured. The pulse wave amplitude is corrected by using the measured pressure change property, and a predetermined algorithm is applied to the corrected value of the pulse wave amplitude so that a blood pressure value is calculated.

A constitution and an operation of the sphygmomanometer 1 according to one or more embodiments of the present invention will be described concretely below.

(With Regard to Hardware Configuration)

Figure 4:
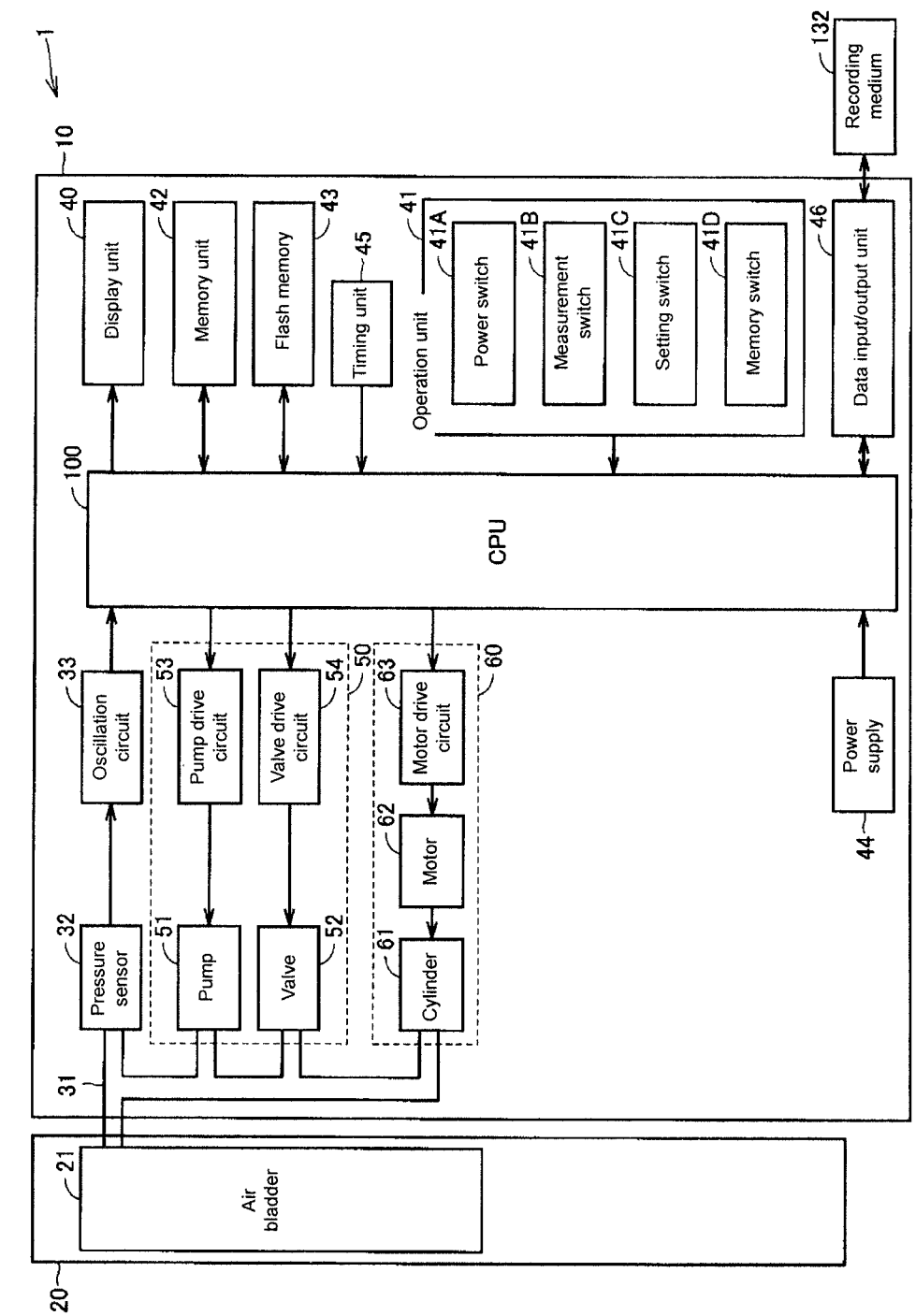
FIG. 4 is a block diagram illustrating a hardware configuration of the electronic sphygmomanometer according to one or more embodiments of the present invention.

FIG. 4 is a block diagram illustrating the hardware configuration of the sphygmomanometer 1 according to one or more embodiments of the present invention.

With reference to FIG. 4, the cuff 20 of the sphygmomanometer 1 includes an air bladder 21. The air bladder 21 is connected to an air system 30 via the air tube 31.

The main body portion 10 includes the display unit 40, the operation unit 41, the air system 30, a CPU (Central Processing Unit) 100 for intensively controlling respective sections and executing various arithmetic processes, a memory unit 42 for storing programs for allowing the CPU 100 to perform predetermined operations and various data, a nonvolatile memory (for example, a flash memory) 43 for storing the measured blood pressure, a power supply 44 for supplying a power to the CPU 100, a timing unit 45 for performing a timing operation, and a data input/output unit 46 for accepting data input from an outside.

The air system 30 includes a pressure sensor 32 for detecting a pressure (cuff pressure) in the air bladder 21, a pump 51 for supplying air to the air bladder 21 in order to heighten the cuff pressure, and a valve 52 that is opened and closed in order to exhaust or seal the air out from or into the air bladder 21.

The main body portion 10 further includes an oscillation circuit 33, a pump drive circuit 53, and a valve drive circuit 54 with relation to the air system 30.

The pressure sensor 32 is, for example, an electrostatic capacity type pressure sensor, and its capacity value changes with the cuff pressure. The oscillation circuit 33 outputs a signal of an oscillation frequency according to the capacity value of the pressure sensor 32 to the CPU 100. The CPU 100 converts a signal acquired from the oscillation circuit 33 into a pressure and detects the pressure. The pump drive circuit 53 controls drive of the pump 51 based on a control signal given from the CPU 100. The valve drive circuit 54 controls opening/closing of the valve 52 based on a control signal given from the CPU 100.

The pump 51, the valve 52, the pump drive circuit 53 and the valve drive circuit 54 constitute an adjustment unit 50 for adjusting the cuff pressure. The devices for adjusting the cuff pressure are not limited to these.

The data input/output unit 46 reads and writes programs and data from and into a detachable recording medium 132, for example. Further/or the data input/output unit 46 may transmit/receive the programs and data from an external computer, not shown, via a communication line.

The above constitution is similar to that of a conventional and general electronic sphygmomanometer. In accordance with one or more embodiments of the present invention, the main body portion 10 further includes a causing unit 60 for causing the constant volume change in the cuff 20. The causing unit 60 has a cylinder 61 for adjusting the volume in the cuff 20 at high speed, a motor (for example, a stepping motor) 62 for driving the cylinder 61, and a motor drive circuit 63 for driving the motor 62.

The cylinder 61 is connected to the air bladder 21 via the air tube 31. The motor 62 operates a piston (not shown) in the cylinder 61 to an axial direction of the cylinder 61. As a result, the volume in the cylinder 61 changes. Accordingly, the volume in the air bladder 21 changes.

The devices constituting the causing unit 60 are not limited to these devices as long as the constant volume change can be caused.

The cuff 20 includes the air bladder 21, but a fluid supplied to the cuff 20 is not limited to air, and thus may be a liquid or gel. Instead of the fluid, uniform fine particles such as microbeads may be used.

(With Regard to Functional Constitution)

Figure 5:
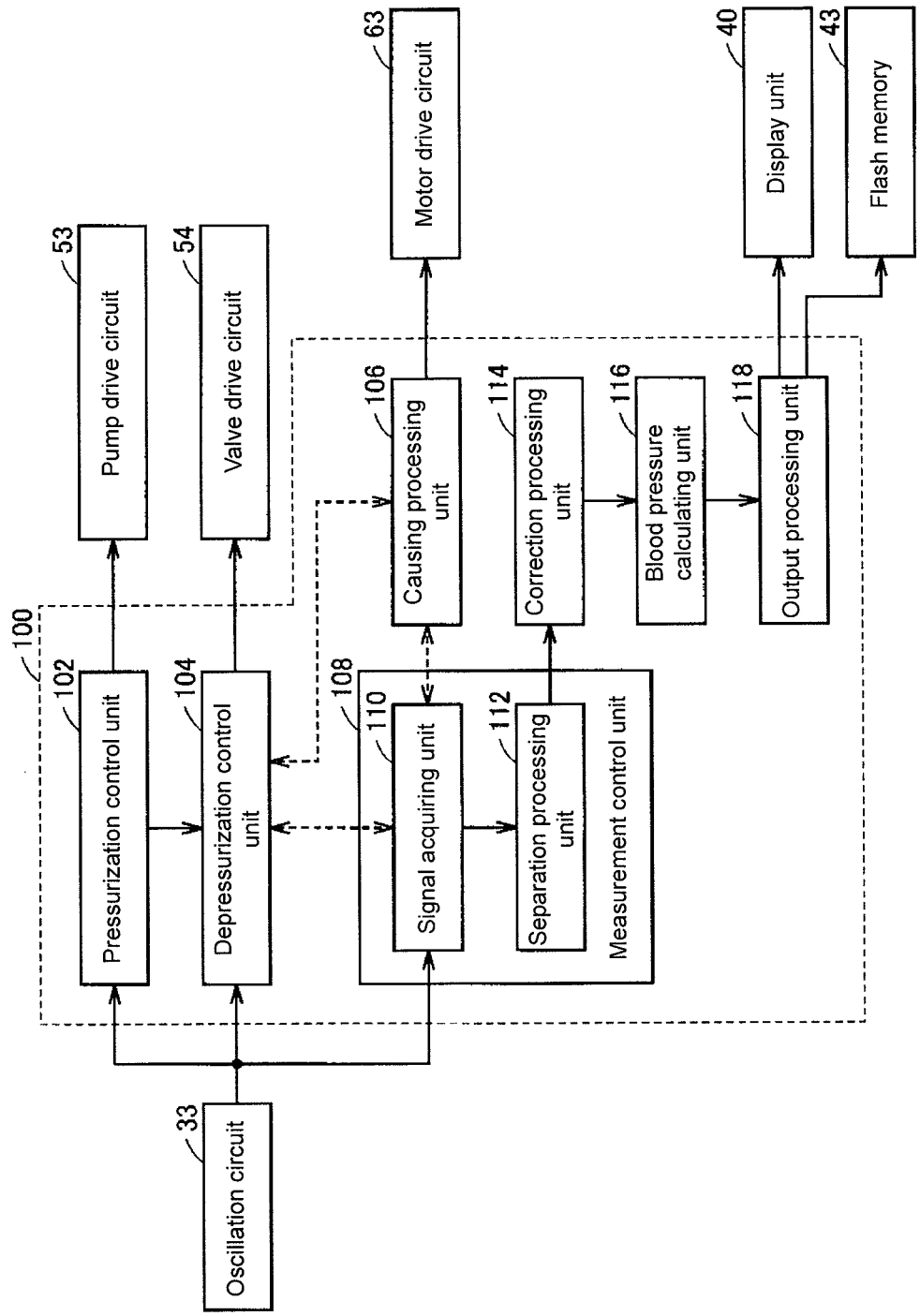
FIG. 5 is a functional block diagram illustrating a functional constitution of the electronic sphygmomanometer according to one or more embodiments of the present invention.

FIG. 5 is a functional block diagram illustrating a functional constitution of the sphygmomanometer 1 according to one or more embodiments of the present invention. FIG. 5 illustrates the functional constitution of a depressurization measurement method, namely, a method for calculating a blood pressure value based on a cuff pressure signal acquired at the time of depressurization.

With reference to FIG. 5, the CPU 100 includes, as its functions, a pressurization control unit 102, a depressurization control unit 104, a causing processing unit 106, a measurement control unit 108, a correction processing unit 114, a blood pressure calculating unit 116, and an output processing unit 118. FIG. 5 illustrates only peripheral hardware that directly transmits/receives signals to/from the respective units of the CPU 100 in order to simplify the description.

The pressurization control unit 102 controls the pressurization of the cuff 20. Concretely, a control signal is transmitted to the pump drive circuit 53, so that the pump 51 is driven and air is sent to the air bladder 21.

The depressurization control unit 104 controls depressurization of the cuff 20 at, for example, a predetermined speed. Concretely, a control signal is transmitted to the valve drive circuit 54, so that the valve 52 is driven and air fed to the air bladder 21 is sealed and exhausted.

In accordance with one or more embodiments of the present invention, the depressurization control means control that changes the pressure in the cuff 20 to a specified direction (namely, a falling direction), and the pressurization control means control that changes the pressure in the cuff 20 to a direction opposite to the specified direction (namely, a rising direction).

The causing processing unit 106 controls the drive of the causing unit 60 (the motor drive circuit 63) for a period of the depressurization control so that a process for causing the constant volume change in the cuff 20 (the air bladder 21) is executed. In accordance with one or more embodiments of the invention, the volume change is caused successively during the depressurization control at a cycle different from a cycle of a heart rate of the person to be measured. The heart rate of the person to be measured may be calculated by a publicly-known method, for example, at the time of the pressurization control, or a past (for example, previous) measured result may be used. In another manner, a numerical value that is not present as the cycle of the heart rate may be preset as the cycle different from the cycle of the heart rate of an examinee.

The measurement control unit 108 makes control based on the cuff pressure signal (detected by the pressure sensor 32) acquired from the oscillation circuit 33 so that the pulse wave amplitude and the pressure change property with respect to the constant volume change are measured. In accordance with one or more embodiments of the invention, the measurement control unit 108 includes a signal acquiring unit 110 and a separation processing unit 112.

The signal acquiring unit 110 acquires the cuff pressure signals in chronological order for the period of the depressurization control. During this period, because the constant volume change is caused in the air bladder 21, the cuff pressure signals acquired for the period of the depressurization control are signals obtained by synthesizing the pulse wave amplitude with the pressure change amplitude with respect to the constant volume change. That is to say, not only a change in an internal pressure of a blood vessel but also the pressure change with respect to the constant volume change are overlapped on the cuff pressure signal detected by the pressure sensor 32.

The separation processing unit 112 executes a filter process on the cuff pressure signal acquired by the signal acquiring unit 110 so as to separate the cuff pressure signal into the pulse wave amplitude and the pressure change property.

The correction processing unit 114 corrects the pulse wave amplitude measured based on the measured pressure change property. The blood pressure calculating unit 116 calculates a blood pressure value, such as, a highest blood pressure and a lowest blood pressure based on the corrected pulse wave amplitude. The output processing unit 118 executes a process for outputting the blood pressure value. For example, the blood pressure value is displayed on the display unit 40, and the blood pressure value is stored in the flash memory 43.

The operations of the above-described functional blocks may be realized by executing software stored in the memory unit 42, or at least one of the functional blocks may be realized by hardware.

Concept of a blood pressure measuring method according to one or more embodiments of the invention will be described with reference to FIGS. 6(A) to 6(F). FIGS. 6(A) to 6(F) are diagrams illustrating the concept of the blood pressure measuring method according to one or more embodiments of the present invention.

Figure 6:
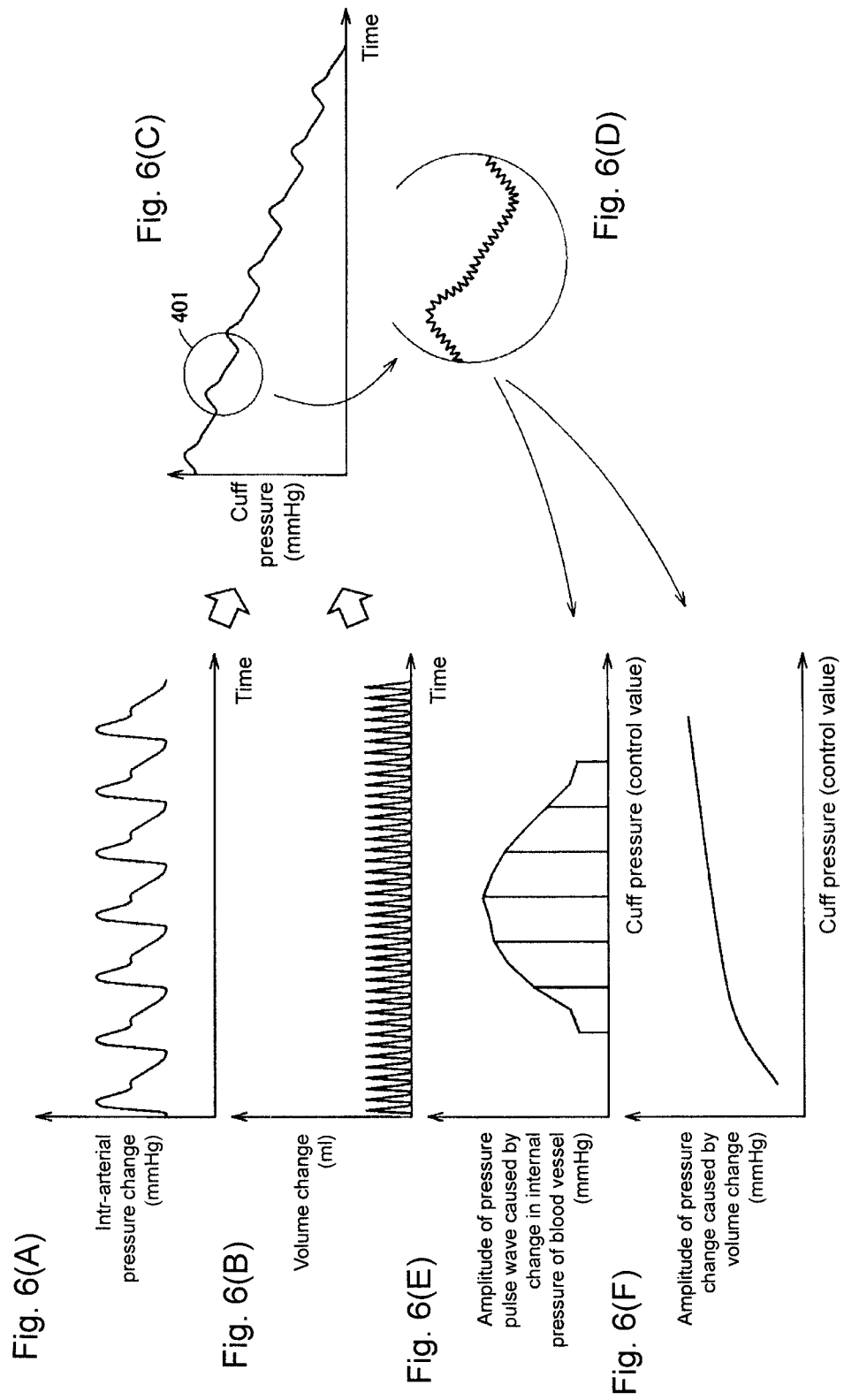
FIGS. 6(A) to 6(F) are diagrams illustrating a concept of a blood pressure measuring method according to the one or more embodiments of the present invention.

FIG. 6(A) illustrates a change in an intra-arterial pressure along a temporal axis. FIG. 6(B) illustrates a volume change along the same temporal axis as that in FIG. 6(A). In accordance with one or more embodiments of the present invention, the constant volume change shown in FIG. 6(B) is given to the cuff 20 during the depressurizing of the cuff 20. In this case, the cuff pressure signal acquired via the oscillation circuit 33 has a waveform as shown in FIGS. 6(C) and 6(D). FIG. 6(D) illustrates a partially enlarged diagram of a part 401 of the cuff pressure signal in FIG. 6(C). As shown in FIG. 6(D), the pressure change with respect to the constant volume change is overlapped with the cuff pressure signal.

In accordance with one or more embodiments of the present invention, the cuff pressure signal including the pressure change with respect to the constant volume change is subject to, for example, the filter process so as to be separated into the pulse wave amplitude (FIG. 6(E)) caused by the change in the internal pressure in the blood vessel and the pressure change amplitude caused by the constant volume change, namely, the pressure change property (FIG. 6(F)).

The concrete correcting method in the correction processing unit 114 will be described later.

(With Regard to Operation)

Figure 7:
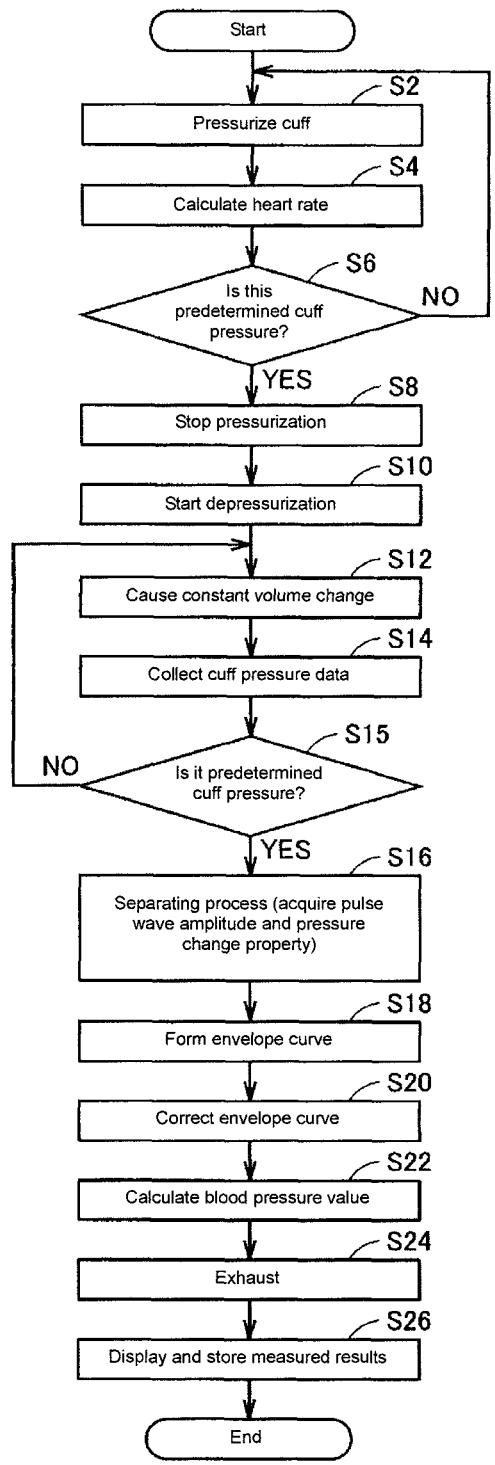
FIG. 7 is a flowchart illustrating a blood pressure measuring process according to one or more embodiments of the present invention.

FIG. 7 is a flowchart illustrating a blood pressure measuring process according to one or more embodiments of the present invention. The process shown in the flowchart in FIG. 7 is stored as a program in the memory unit 42 in advance. The CPU 100 reads and executes this program so that the function of the blood pressure measuring process is realized.

With reference to FIG. 7, the pressurization control unit 102 pressurizes the cuff 20 (step S2). During the pressurization, the pressurization control unit 102 calculates a heart rate based on an output from the oscillation circuit 33 by a publicly-known method (step S4).

The pressurization control unit 102 determines whether the pressure in the cuff 20 (the cuff pressure) is a predetermined value (for example, 200 mmHg) (step S6). When the determination is made that the cuff pressure does not reach the predetermined value (NO in step S6), the sequence returns to step S2, and the above process is repeated. When the determination is made that the cuff pressure reaches the predetermined value (YES in step S6), the pressurization is stopped (step S8). In accordance with one or more embodiments of the present invention, the pressurization is stopped when the cuff pressure reaches the predetermined value, but at the time when the highest blood pressure is estimated during the pressurization, the pressurization may be stopped like a conventional method.

The depressurization control unit 104 then starts to depressurize the cuff 20 (step S10). At the same time, the causing processing unit 106 causes the constant volume change in the cuff 20 (step S12). Concretely, a control signal is transmitted to the motor drive circuit 63, so that the cylinder 61 is driven at a high speed, and the constant volume change is given to the air bladder 21. A cycle different from that of the heart rate of the person to be measured calculated in step S4 is selected as the cycle of the volume change.

The signal acquiring unit 110 of the measurement control unit 108 acquires cuff pressure data (the cuff pressure signal) detected by the pressure sensor 32 during the depressurization (step S14). The acquired cuff pressure data is stored in the memory unit 42 in chronological order.

The depressurization control unit 104 then determines whether the cuff pressure reaches a predetermined value (for example, 40 mmHg) (step S15). When the determination is made that the cuff pressure does not reach the predetermined value (NO in step S15), the sequence returns to step S12, and the above process is repeated. When the determination is made that the cuff pressure reaches the predetermined value (YES in step S15), the depressurization control is ended and the sequence goes to step S16. In accordance with one or more embodiments of the present invention, when the cuff pressure reaches the predetermined value, the depressurization control is ended, but at the time when the blood pressure can be calculated (for example, at the time of the lowest blood pressure value estimated during the pressurization or less, at the time when the amplitude is smaller than a predetermined value or the like), the depressurization control may be ended.

In step S16, the separation processing unit 112 of the measurement control unit 108 filtrates the cuff pressure data acquired in chronological order in step S14 to separate the data into the pulse wave amplitude and the pressure change property. Concretely, for example, a filter process for eliminating a high-frequency component from the cuff pressure data and a filter process for extracting the high-frequency component are executed in parallel. As a result, the pulse wave amplitude and the pressure change property can be extracted.

Thereafter, the correction processing unit 114 corrects the pulse wave amplitude acquired in step S16. Concretely, an envelope curve of a value string of the pulse wave amplitude is formed (step S18), and the formed envelope curve is corrected by using the pressure change property obtained in step S16 (step S20). Such a process for correcting the pulse wave amplitude will be described in detail with reference to FIG. 8.

FIGS. 8(A) to 8(D) are diagrams for describing the process for correcting the pulse wave amplitude according to one or more embodiments of the present invention.

Figure 8A:
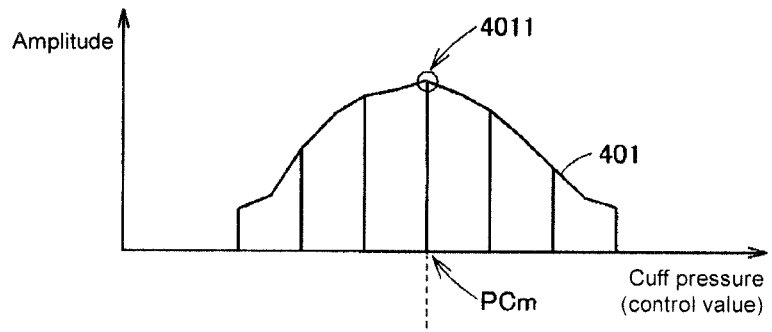
FIGS. 8(A) to 8(D) are diagrams for describing a process for correcting a pulse wave amplitude according to one or more embodiments of the present invention.
Figure 8B:
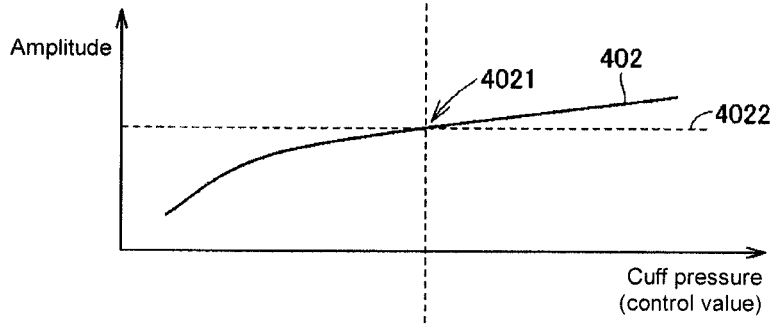

FIG. 8(A) illustrates an example of the envelope curve 401 formed in step S18. FIG. 8(B) illustrates an example of a line representing the pressure change property acquired in step S16 (hereinafter, "characteristic line") 402.

Figure 8C:
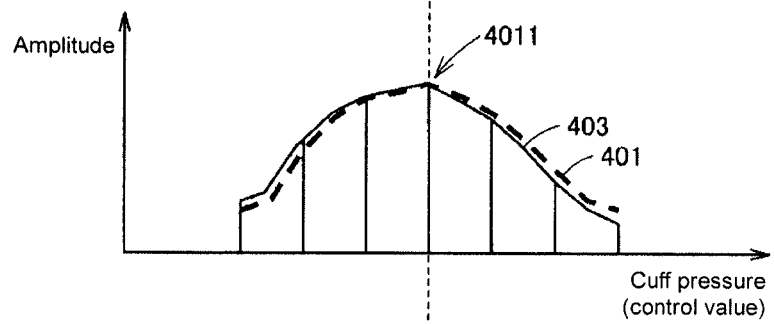

The correction processing unit 114 detects the cuff pressure PCm corresponding to a maximum point 4011 of the envelope curve 401. The cuff pressure PCm corresponds to an average blood pressure (MAP). The correction processing unit 114 uses a point 4021 corresponding to the cuff pressure PCm on the characteristic line 402 as a standard, and corrects the envelope curve 401 so that characteristic line 402 has a constant amplitude. That is to say, the envelope curve 401 is corrected so that the characteristic line 402 becomes a straight line 4022 passing through the point 4021. FIG. 8(C) illustrates a corrected envelope curve 403. In the corrected envelope curve 403, a side lower than the cuff pressure PCm is revised upward, and a side lower than the cuff pressure PCm is revised downward.

Figure 8D:
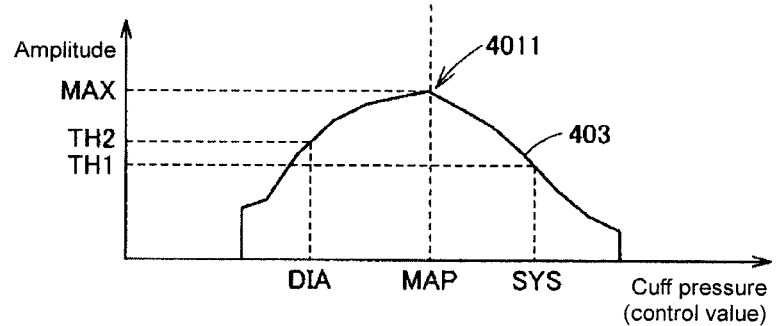

With reference to FIG. 7 and FIG. 8(D), the blood pressure calculating unit 116 calculates a highest blood pressure (SYS) and a lowest blood pressure (DIA) (step S22) based on the corrected envelope curve 403. Concretely, the calculation is carried out in the following manner. That is to say, a value obtained by multiplying the maximum point 4011 of the envelope curve 403 by a predetermined constant (for example, 0.5) is determined as a threshold TH1, and a value obtained by multiplying the maximum point 4011 by a predetermined constant (for example, 0.7) is determined as the threshold TH2. The cuff pressure that is higher than the average blood pressure (MAP) and corresponds to a point at which the corrected envelope curve 403 and the threshold TH1 intersect is determined as the highest blood pressure (SYS). The cuff pressure that is lower than the average blood pressure (MAP) and corresponds to a point at which the corrected envelope curve 403 and the threshold TH2 intersect is determined as the lowest blood pressure (DIA).

The blood pressure calculating unit 116 may calculate a heart rate based on the pulse wave amplitude acquired by the separating process according to a publicly-known method.

Finally, air is exhausted from the air bladder 21 (step S24), and the output processing unit 118 displays and records measured results (the highest blood pressure, the lowest blood pressure and the heart rate) (step S26). The flash memory 43 stores measurement data in which, for example, the measured values (the highest blood pressure, the lowest blood pressure, and the heart rate) are related to measurement time and dates in a record format.

The blood pressure measuring process according to one or more embodiments of the present invention is ended with the above-described manner. The exhausting process (step S24) may be executed in parallel with the process in steps S16 to S22.

As described above, according to one or more embodiments of the present invention, the pressure change property is extracted at every measurement. For this reason, influences of the wrapping state of the cuff 20 and secular changes in the pump 51, the valve 52 and the cuff 20 are securely reflected on the pressure change property. In accordance with one or more embodiments of the present invention, the pulse wave amplitude caused by the change in the internal pressure in the blood vessel is corrected based on such a pressure change property, and the blood pressure value is calculated. Therefore, the blood pressure value can be accurately measured regardless of the wrapping state of the cuff 20 and the secular changes in the pump 51, the valve 52 and the cuff 20.

In accordance with one or more embodiments, the envelope curve is formed based on the waveform (the pulse wave amplitude) from which the influence of the pressure change with respect to the constant volume change is eliminated by filtration, but may be formed based on the amplitude of the cuff pressure signal before filtration.

Embodiments described above with respect to the first example describe a depressurization measuring method as the example, but one or more embodiments of the present invention can be applied also to the pressurization measuring method. In this case, the constant volume change is caused during a period of the pressurization control, and the cuff pressure signal may be acquired during the period of the pressurization control.

Second Example

One or more embodiments of a second example of the present invention will be described below.

As described above, in accordance with one or more embodiments of the present invention the constant volume change is caused at a cycle different from that of a heart rate of a person to be measured during the period of the pressure control (the depressurization control) for which the pulse wave amplitude is measured. The cuff pressure data, in which the pressure change is overlapped with the constant volume change, is subject to the filter process, so that the pressure change property is extracted.

However, in accordance with one or more embodiments of the present invention, the constant volume change is caused at a constant interval (successively) during the period of the pressure control for which the pulse wave amplitude is measured. Amplitude values of the cuff pressure signal are measured when the volume change is caused and is not caused, so that the pressure change property is measured without the filter process.

In accordance with one or more embodiments of the present invention, the stepwise pressure control (so-called step depressurization) is made so that the cuff pressure signals at the times when the constant volume is caused and is not caused are measured when the pressure values in the cuff are equal. The pulse wave amplitude and the pressure change property are calculated based on the two kinds of measured cuff pressure signals.

Figure 9A:
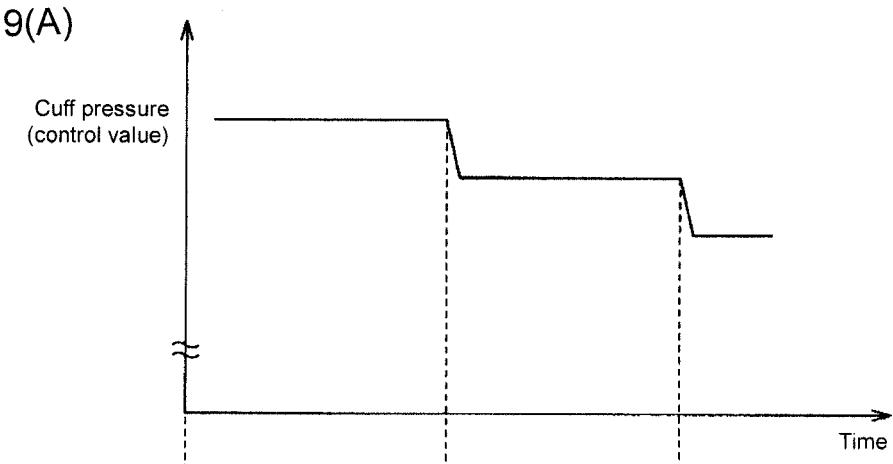
FIGS. 9(A) and 9(B) are diagrams illustrating detection timings of a pulse wave amplitude and a pressure change property according to one or more embodiments of the present invention.
Figure 9B:
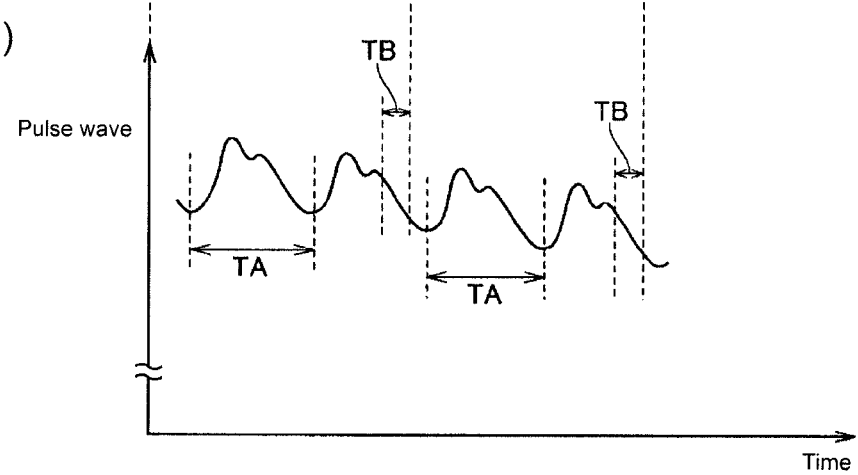

FIGS. 9(A) and 9(B) are diagrams illustrating detection timings of the pulse wave amplitude and the pressure change property according to one or more embodiments of the present invention. FIG. 9(A) illustrates the cuff pressure as the control value along a temporal axis. FIG. 9(B) illustrates the cuff pressure signal (mainly, a pulse wave) along the same temporal axis as that of FIG. 9(A). In FIG. 9(B), a segment TA is a period for which the pulse wave is detected. That is to say, the segment TA represents a detection period of the cuff pressure signal to be used for calculation of the pulse wave amplitude. A segment TB is a period for which the constant volume change is caused. Therefore, the segment TB represents the detection period of the cuff pressure signal to be used for the calculation of the pressure change property.

In accordance with one or more embodiments of the present invention, the segment TA is a segment from start to end of one beat of a pulse wave (a rising point of the pulse wave to a rising point of next pulse wave), and the segment TB is a partial segment of next pulse wave in the segment TA.

In such a manner, the constant volume change is caused on the same position at every time in the same cycle as that of the heart rate of the person to be measured, so that the pressure change property (the line representing this) can be obtained.

The segment TA may include at least the rising point of one beat of a pulse wave or the rising point of next pulse wave, and a maximum point of the pulse wave therebetween. The segment TB may be a segment that does not include the rising point of one beat of a pulse wave, the rising point of next pulse wave and the maximum point of the pulse wave therebetween. Therefore, when the segment TA includes the rising point of one beat of a pulse wave through the rising point of next pulse wave as shown in FIG. 9(B), the segment TB may be included in the segment TA. That is to say, in accordance with one or more embodiments of the present invention, the pulse wave amplitude and the pressure change property are measured in series but may be measured in parallel.

The period represented by the segment TB is the time shorter than the cycle of the heart rate and may be predetermined, or determined at every measurement.

As shown in FIG. 9(A), the pressure in the cuff is maintained until the pulse wave amplitude and the pressure change property are measured (more specifically, the cuff pressure data that can be used for the calculation of the pulse wave amplitude and the pressure change property is collected). When the pulse wave amplitude and the pressure change property are measured, the depressurization to a predetermined pressure is carried out. As a result, the pulse wave amplitude and the pressure change property can be acquired for the depressurization period without filtrating the cuff pressure signal.

Figure 10A:
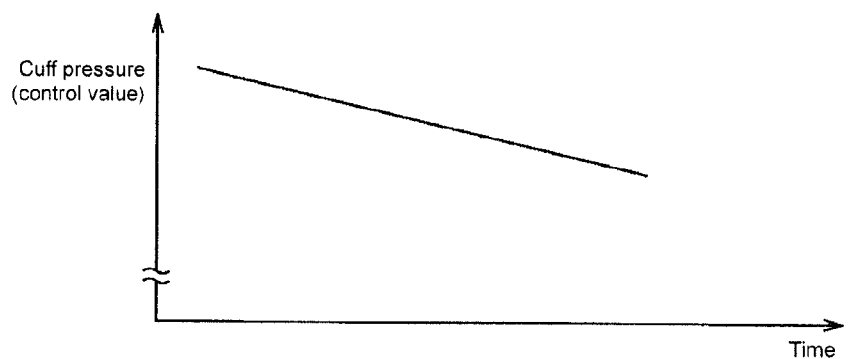
FIGS. 10(A) and 10(B) are diagrams illustrating another examples of the detection timings of the pulse wave amplitude and the pressure change property according to one or more embodiments of the present invention.
Figure 10B:
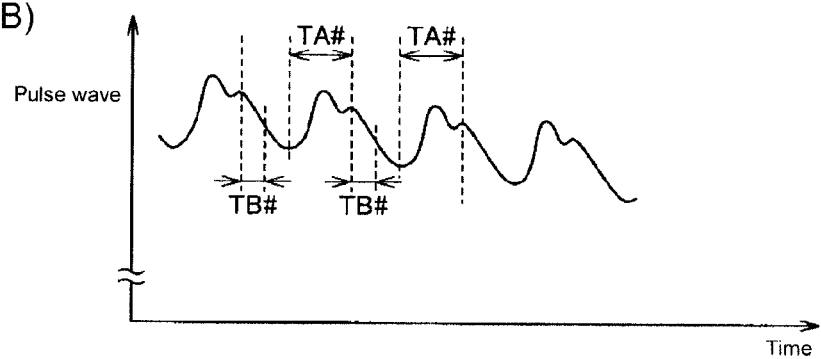

In order to acquire the pulse wave amplitude and the pressure change property, it is not necessary to carry out such step depressurization. As shown in FIGS. 10(A) and 10(B), both of them may be detected at every pulse at a predetermined speed during the depressurization. FIG. 10(A) illustrates the cuff pressure as the control value along a temporal axis. FIG. 10(B) illustrates the cuff pressure signal (mainly, the pulse wave) along the same temporal axis as that in FIG. 10(A). As shown in FIG. 10(B), a segment from the rising point of one beat of a pulse wave to the maximum point may be represented by a segment TA# (a period for detecting the pulse wave), and at least a partial segment from the maximum point of the pulse wave to the rising point of next pulse wave may be represented by a segment TB# (a period for causing the constant volume change).

The constitution and the basic operation of the sphygmomanometer in accordance with embodiments of the second example are similar to the embodiments in the first example. Therefore, the description uses reference symbols used with respect to the first example is given.

Only portions different from the first example will be described below.

(With Regard to Functional Constitution)

Figure 11:
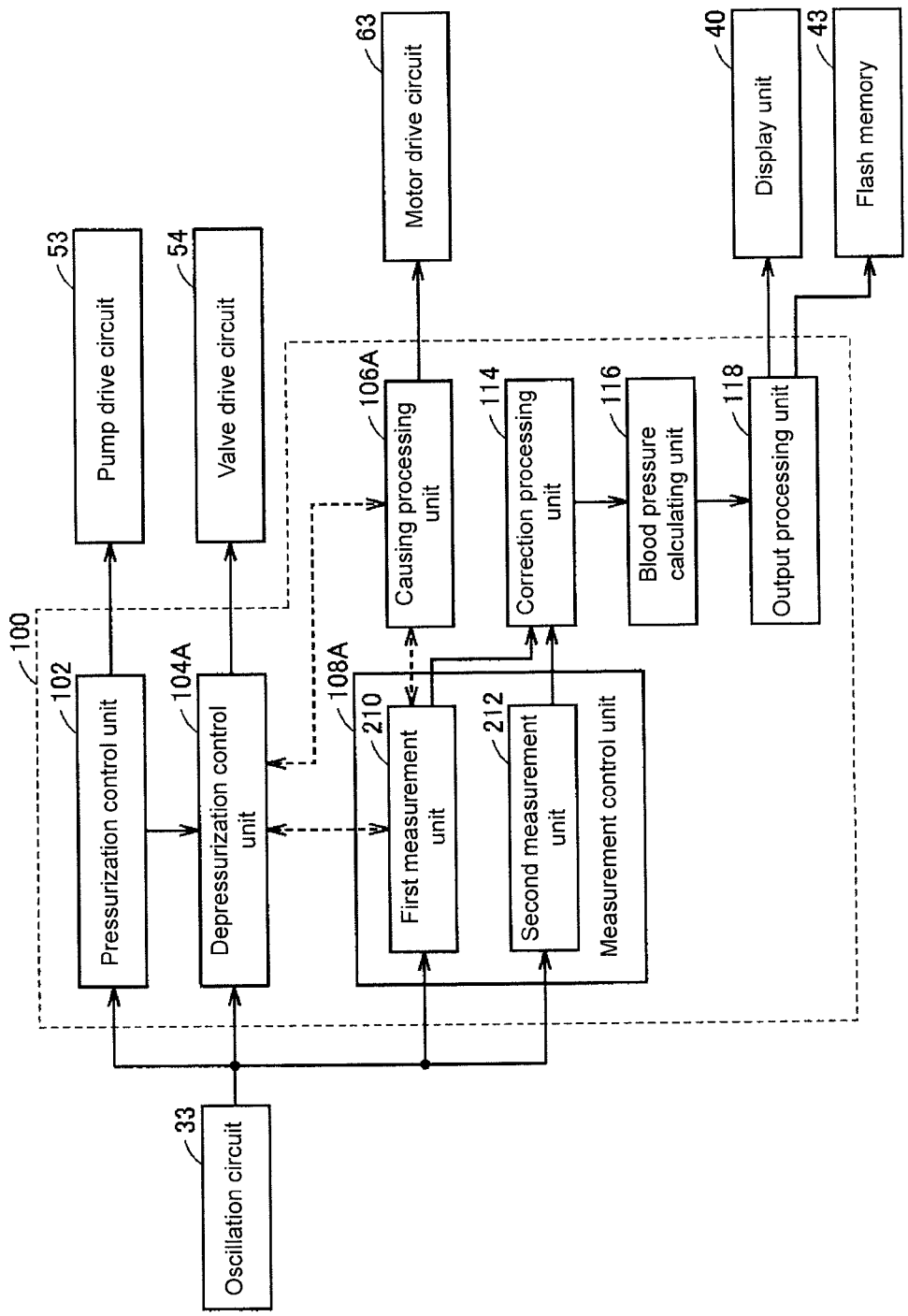
FIG. 11 is a functional block diagram illustrating a functional constitution of the electronic sphygmomanometer according to one or more embodiments of the present invention.

FIG. 11 is a functional block diagram illustrating a functional constitution of the sphygmomanometer 1 according to one or more embodiments of the present invention. FIG. 11 also illustrates a functional constitution of the depressurizing measuring method. Functional blocks that execute the similar processes to those in the functional blocks shown in FIG. 5 are denoted by the same reference symbols. Therefore, the description thereof will not be repeated.

With reference to FIG. 11, in accordance with one or more embodiments of the second example, the CPU 100 includes a depressurization control unit 104A, a causing processing unit 106A and a measurement control unit 108A instead of the depressurization control unit 104, the causing processing unit 106 and the measurement control unit 108 as previously described.

The depressurization control unit 104A makes the stepwise depressurization control, namely, the step depressurization. The causing processing unit 106A causes the constant volume change at a constant interval during the period of the depressurization control. In accordance with one or more embodiments of the present invention, start timing at which the constant volume change is caused is preferably the same cycle as that of the heart rate of the person to be measured.

The measurement control unit 108A includes a first measurement unit 210 and a second measurement unit 212 instead of the signal acquiring unit 110 and the separation processing unit 112. The first measurement unit 210 measures the pressure change property based on the cuff pressure signal output at the specified segment (the segment TB in FIG. 9) where the constant volume change is given to the cuff 20. The second measurement unit 212 measures the pulse wave amplitude based on the cuff pressure signal output at the period of the depressurization control and at a segment other than the specified segment (namely, a segment where the constant volume change is not caused (the segment TA in FIG. 9)).

(With Regard to Operation)

Figure 12:
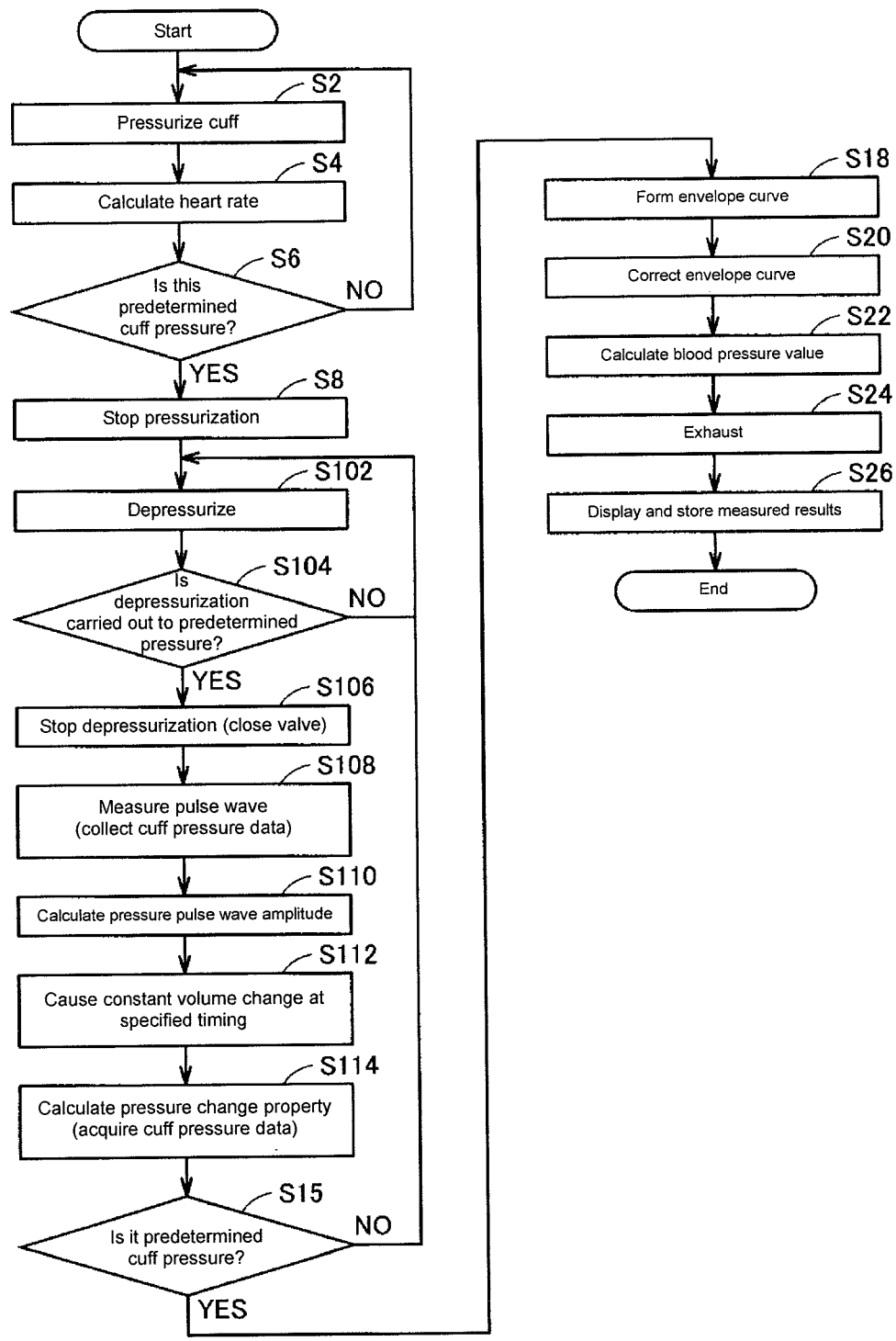
FIG. 12 is a flowchart illustrating the blood pressure measuring process according to one or more embodiments of the present invention.

FIG. 12 is a flowchart illustrating the blood pressure measuring process according to one or more embodiments of the second example of the present invention. The processes similar to those in the flowchart in FIG. 7 are denoted by the same step numbers. Therefore, the description thereof will not be repeated.

With reference to FIG. 12, in comparison with the flowchart in FIG. 7, the processes in steps S102 to S114 are inserted between step S8 and step S15 instead of steps S10 to S14. Further, step S16 is deleted.

In accordance with one or more embodiments of the present invention, when the processes in steps S2, S4, S6 and S8 are executed, the depressurization control unit 104A opens the valve 54 so as to depressurizes the cuff 20 (step S102). The depressurization control unit 104A determines whether the pressure at the start of the depressurization is depressurized to predetermined pressure (step S104). The cuff 20 is depressurized until a pressure difference reaches predetermined pressure (NO in step S104). When the pressure difference reaches the predetermined pressure (YES in step S104), the depressurization is stopped (step S106). That is to say, the valve 54 is closed.

The second measurement unit 212 acquires the cuff pressure signal so as to measure the pulse wave (step S108) and calculate the pulse wave amplitude (step S110). The measurement period of the pulse wave is a period from the stop of the depressurization to detection of the rising point of next pulse wave as represented by the segment TA in FIG. 9(B).

Thereafter, when the maximum point of next pulse wave is detected, the causing processing unit 106A causes the constant volume change in the cuff 20 for a constant period (the segment TB in FIG. 9(B)) at specified timing (for example, predetermined msec time elapses after the maximum point of the pulse wave) (step S112). The pressure change amplitude with respect to the constant volume change is measured based on the cuff pressure signal detected for the period (the segment TB) for which the volume change is being caused, so that the pressure change property is calculated (step S114).

The depressurization control unit 104A determines whether the cuff pressure reaches the predetermined value as described above (step S15). Steps S102 to S114 are repeated until the cuff pressure reaches the predetermined value (NO in step S15). When the determination is made that the cuff pressure reaches the predetermined value (YES in step S15), the sequence goes to step S18.

In such a manner, in accordance with one or more embodiments of the present invention, because the period for which the constant volume change is caused is limited to a constant segment (the segment TB), the separating process in step S16 as described above is not necessary.

In accordance with one or more embodiments of the present invention, in steps S18 and S20, the correction processing unit 114 forms an envelope curve based on the pulse wave amplitude calculated in step S110, and corrects the formed envelope curve using the pressure change property calculated in step S114. The correcting method is similar to that described previously herein.

In accordance with one or more embodiments of the present invention, the pulse wave amplitude and the pressure change property (the pressure change amplitude with respect to the constant volume change) are calculated during the depressurization control, but they may be calculated after the end of the depressurization control. That is to say, when the cuff pressure signal measured during the depressurization control is used for the calculation of the pulse wave amplitude and the pressure change property, their calculation timings are not considered.

Third Example

Embodiments in accordance with a third example of the present invention will be described below.

In embodiments of the first and second examples, the constant volume change is caused successively or intermittently during the pressure control (the depressurization control) for measuring the pulse wave amplitude. However, in accordance with one or more embodiments of the third example, the pressure change property is measured for the period different from the period of the pressure control for measuring the pulse wave amplitude.

Figure 13:
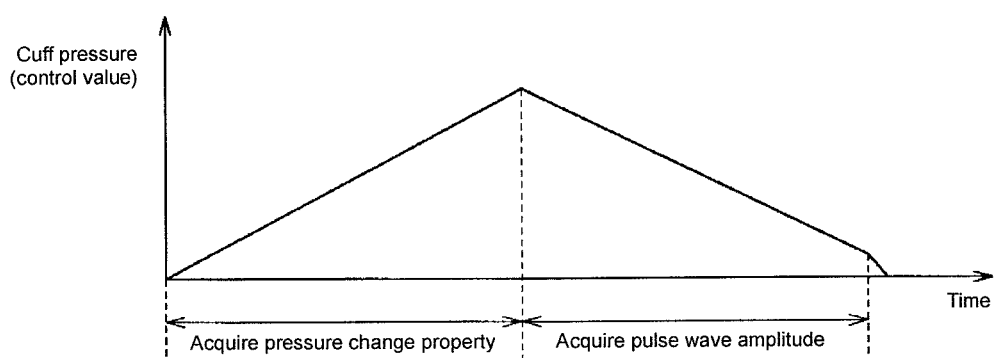
FIG. 13 is a diagram illustrating the detection timings of the pulse wave amplitude and the pressure change property according to one or more embodiments of the present invention.

FIG. 13 is a diagram illustrating the detection timings of the pulse wave amplitude and the pressure change property according to one or more embodiments of the present invention. FIG. 13 illustrates the cuff pressure as the control value along a temporal axis. In accordance with one or more embodiments of the present invention, for example, the pressure change property is acquired for the pressurization period, and the pulse wave amplitude is acquire for the depressurization period. In accordance with one or more embodiments the pressurization speed is equal to the depressurization speed.

Only portions different from the previous embodiments will be described below.

(With Regard to Hardware Configuration)

Figure 14:
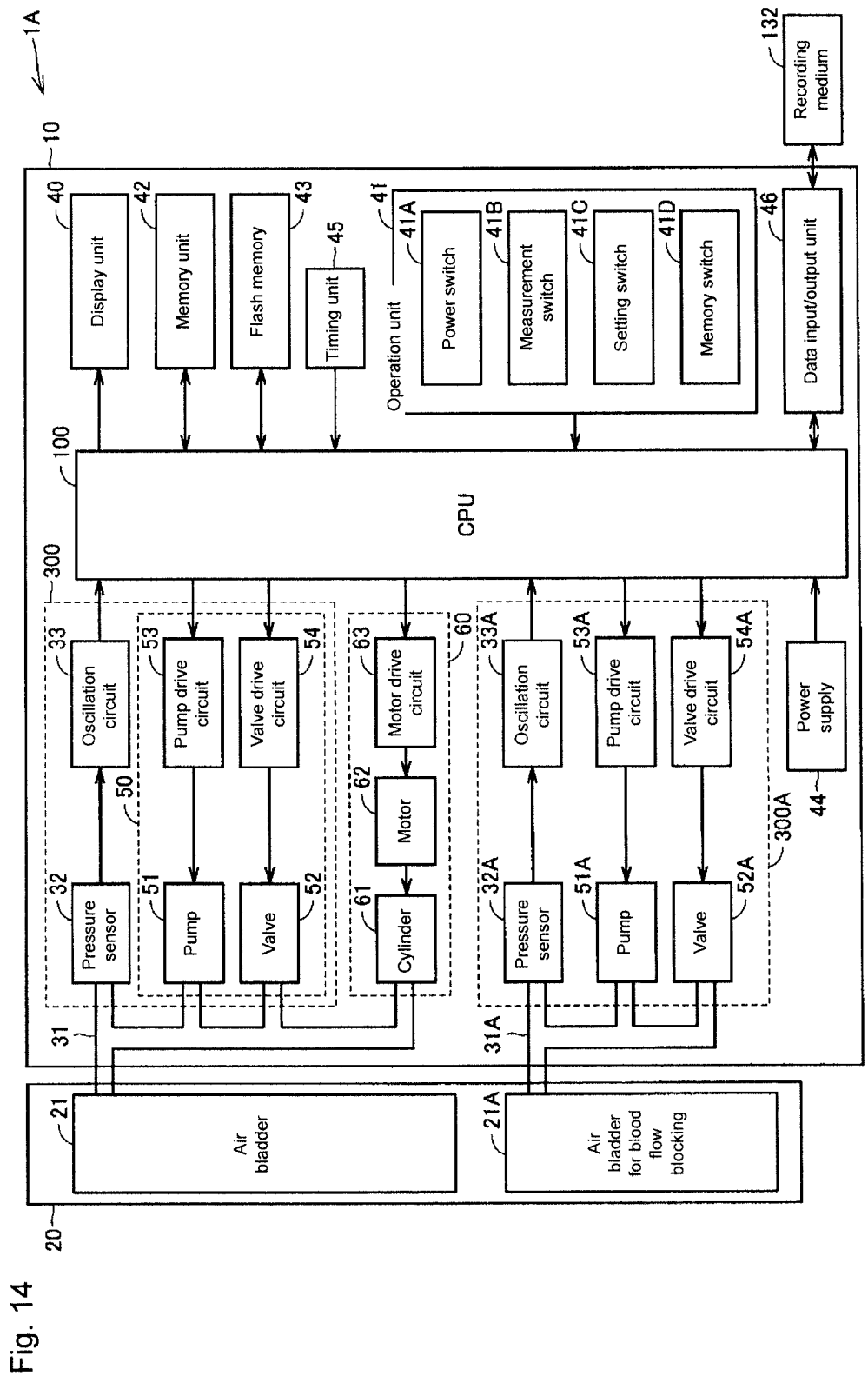
FIG. 14 is a block diagram illustrating a hardware configuration of the electronic sphygmomanometer according to one or more embodiments of the present invention.

FIG. 14 is a block diagram illustrating a hardware configuration of a sphygmomanometer 1A according to one or more embodiments of the present invention. The same components as those shown in FIG. 4 are denoted by the same reference symbols. Therefore, the description thereof is not repeated.

With reference to FIG. 14, the cuff 20 in accordance with one or more embodiments of the present invention includes an air bladder 21A for blood flow blocking as well as the air bladder 21 for the measurement of a blood pressure. The air bladder 21A for blood flow blocking is arranged so as to be located on an upper-stream side of an artery with respect to the air bladder 21 when the cuff 20 is attached to a measurement site.

The pressure sensor 32, the oscillation circuit 33, the pump 51, the valve 52, the pump drive circuit 53 and the valve drive circuit 54 included in the general sphygmomanometer are called as a first adjustment/detection unit 300. In accordance with one or more embodiments of the present invention, the main body portion 10 further includes a second adjustment/detection unit 300A having the same constitution as that of the first adjustment/detection unit 300. The second adjustment/detection unit 300A includes a pressure sensor 32A, an oscillation circuit 33A, a pump 51A, a valve 52A, a pump drive circuit 53A and a valve drive circuit 54A. The pressure sensor 32A, the pump 51A and the valve 52A are connected to the air bladder 21A for blood flow blocking via the air tube 31A. Operations of respective section in the second adjustment/detection unit 300A are similar to the operations of the respective sections in the first adjustment/detection unit 300.

In accordance with one or more embodiments of the present invention, the air bladder 21A for blood flow blocking is provided to the cuff 20, but not limited to this as long as blood flow is blocked on the measurement site.

(With Regard to Functional Constitution)

Figure 15:
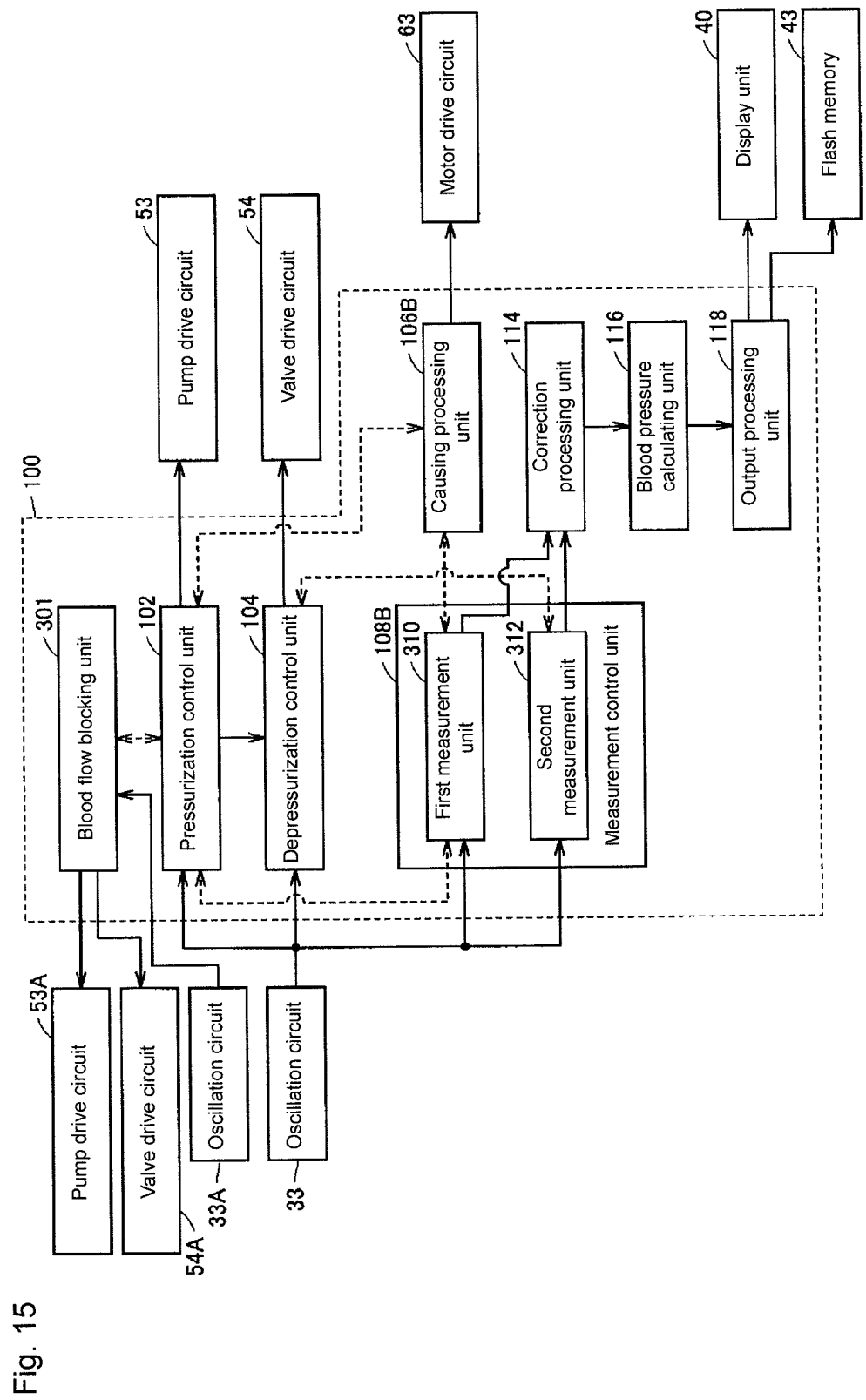
FIG. 15 is a functional block diagram illustrating a functional constitution of the electronic sphygmomanometer according to one or more embodiments of the present invention.

FIG. 15 is a functional block diagram illustrating the sphygmomanometer 1A according to one or more embodiments of the present invention. FIG. 15 also illustrates the functional constitution of the depressurization measuring method. Components that executes the similar processes to those of the functional block shown in FIG. 5 are denoted by the same reference symbols. Therefore, description thereof will not be repeated.

With reference to FIG. 15, in accordance with one or more embodiments of the present invention, the CPU 100 includes a blood flow blocking unit 301. Further, the CPU 100 includes a causing processing unit 106B and a measurement control unit 108B instead of the causing processing unit 106 and the measurement control unit 108 as described above. In accortion, the pressurization control represents control for changing the pressure in the cuff 20 to a specified direction (namely, a rising direction), and the depressurization control represents control for changing the pressure in the cuff 20 to a direction opposite to the specified direction (namely, a falling direction).

The blood flow blocking unit 301 blocks blood flow of the measurement site using the air bladder 21A for blood flow blocking only for the period of the pressurization control. The blood flow blocking unit 301 is connected to the pump drive circuit 53A, the valve drive circuit 54A and the oscillation circuit 33A. While the pressure in the air bladder 21A is being detected via the oscillation circuit 33A, the pump 51A is driven, and when the pressure in the air bladder 21A does not fluctuate, the drive of the pump 51A is stopped.

The causing processing unit 106B causes the constant volume change sequentially during the period of the pressurization control, for example. The cycle of the volume change in accordance with one or more embodiments of the present invention may be a predetermined cycle.

The measurement control unit 108B includes a first measurement unit 310 and a second measurement unit 312. The first measurement unit 310 measures the pressure change property based on the cuff pressure signal output during the period of the pressurization control. The second measurement unit 312 measures the pulse wave amplitude based on the cuff pressure signal output during the period of the depressurization control.

(With Regard to Operation)

Figure 16:
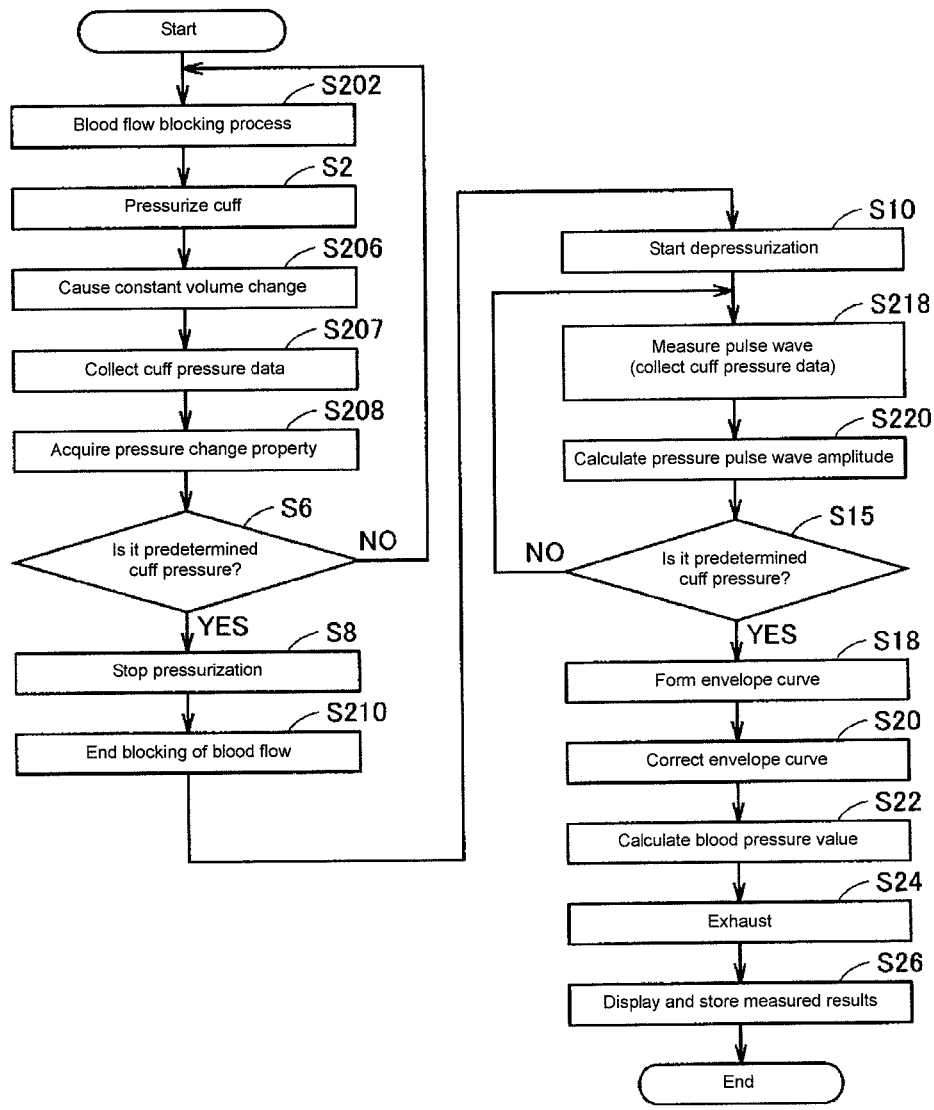
FIG. 16 is a flowchart illustrating the blood pressure measuring process according to one or more embodiments of the present invention.

FIG. 16 is a flowchart illustrating the blood pressure measuring process according to one or more embodiments of the present invention. The processes similar to those in the flowchart in FIG. 7 are denoted by the same step numbers. Therefore, description thereof will not be repeated.

With reference to FIG. 16, in comparison with the flowchart in FIG. 7, a process in step S202 is inserted first, and processes in steps S206, S207 and S208 are inserted between step S2 and step S6 instead of step S4. Further, a process in step S210 is inserted between step S8 and step S10. Further, processes in step S218 and step S220 are executed instead of the processes in step S12 and step S14.

In accordance with one or more embodiments of the present invention, before the start of the pressurization, the blood flow blocking unit 301 expands the air bladder 21A for blood flow blocking so as to execute a process for blocking a blood flow of the measurement site on an upper-stream side pressurized by the air bladder 21 (step S 202). As a result, the pulse wave amplitude is not caused in the air bladder 21 by the intra-arterial pressure change.

When the blood flow of the measurement site is blocked and the cuff is pressurized (step S2), the causing processing unit 106B causes the constant volume change in the air bladder 21 (step S 206). The first measurement unit 310 acquires the cuff pressure signal (the cuff pressure data) via the oscillation circuit 33 (step S207) during the period of the pressurization. The first measurement unit 310 calculates (acquires) the pressure change property from the acquired cuff pressure signal (step S208). In accordance with one or more embodiments of the present invention, because the blood flow on the upper stream side of the air bladder 21 is blocked at the time of the pressurization, the amplitude of the acquired cuff pressure signal can be directly measured as the pressure change property.

When the pressurization is stopped (step S8), the blood flow blocking unit 301 exhausts the air from the air bladder 21A for blood flow blocking so as to end the blood flow blocking (step S 210).

When the depressurization is started (step S10), similarly to the normal blood pressure measuring process, the second measurement unit 312 acquires the cuff pressure signal (the cuff pressure data), namely, a pressure pulse wave via the oscillation circuit 33 (step S 218). The acquired amplitude of the pressure pulse wave (the pulse wave amplitude) is calculated (step S220). In accordance with one or more embodiments of the present invention, because the constant volume change is not caused at the time of the depressurization, the acquired cuff pressure signal represents the pressure pulse wave.

In accordance with one or more embodiments of the present invention, the correction processing unit 114 forms the envelope curve in steps S18 and S20 based on the pulse wave amplitude calculated in step S220, and corrects the formed envelope curve using the pressure change property calculated in step S208. The correcting method itself is similar to that as described above.

In accordance with one or more embodiments of the present invention, the pressure change property (the pressure change amplitude with respect to the constant volume change) and the pulse wave amplitude are calculated during the pressurization control and the depressurization control, respectively. However, their calculating timings are not considered as long as the cuff pressure signals detected during the respective controls are used for the calculation of the pressure change property and the pulse wave amplitude.

While the invention has been described with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

DESCRIPTION OF SYMBOLS 1, 1A: the electronic sphygmomanometer
10: main body portion
20: cuff
21: air bladder (for blood pressure measurement)
21A: air bladder for blood flow blocking
30: air system
31, 31A: air tube
32, 32A: the pressure sensor
33, 33A: oscillation circuit
40: display unit
41: operation unit
41A: power switch
41B: measurement switch
41C: setting switch
41D: memory switch
42: memory unit
43: flash memory
44: power supply
45: timing unit
46: data input/output unit
50: adjustment unit
51, 51A: pump
52, 52A: valve
53, 53A: pump drive circuit
54, 54A: valve drive circuit
60: causing unit
61: cylinder
62: motor
63: motor drive circuit
100: CPU 102: pressurization control unit
104, 104A: depressurization control unit
106, 106A, 106B: causing processing unit
108, 108A, 108B: measurement control unit
110: signal acquiring unit
112: separation processing unit
114: correction processing unit
116: blood pressure calculating unit
118: output processing unit
132: recording medium
210, 310: first measurement unit
212, 312: second measurement unit
300, 300A: adjustment/detection unit
301: the blood flow blocking unit.

The invention claimed is:

1. An electronic sphygmomanometer, comprising:
a cuff capable of being wrapped around a measurement site;
a pressure adjustment unit that adjusts a pressure in the cuff;
a pressure sensor that detects a cuff pressure signal representing the pressure in the cuff;
a causing unit comprising a cylinder, a motor, and a motor drive circuit that causes a constant volume change in the cuff;
a first pressure control unit that controls drive of the pressure adjustment unit so as to make a first pressure control for changing the pressure in the cuff to a specified direction;
a causing processing unit that controls drive of the causing unit for a period for which the first pressure control is made and executes a process for causing the constant volume change in the cuff;
a measurement control unit that controls measurement of a pressure change property with respect to the volume change based on the cuff pressure signal acquired at the time of executing a process of the causing processing unit and measurement of the pulse wave amplitude based on the cuff pressure signal;
a correction processing unit that corrects the pulse wave amplitude based on the measured pressure change property; and
a blood pressure calculating unit that calculates a blood pressure value based on the corrected pulse wave amplitude,
wherein the causing processing unit causes the volume change at a constant interval during the period of the first pressure control, and
wherein the measurement control unit comprises:
a first measurement processing unit that measures the pressure change property based on the cuff pressure signal output at a specified segment where the volume change is given to the cuff, and
a second measurement processing unit that measures the pulse wave amplitude based on the cuff pressure signal output during the period of the first pressure control and at a segment other than the specified segment.

2. The electronic sphygmomanometer according to claim 1,
wherein the causing processing unit causes the volume change successively at a cycle different from that of a heart rate of a person to be measured during a period of the first pressure control, and
wherein the measurement control unit comprises:
an acquiring unit that acquires the cuff pressure signal in chronological order during the period of the first pressure control, and
a separation unit that executes a filter process on the acquired cuff pressure signal so as to separate the acquired cuff pressure signal into the pulse wave amplitude and the pressure change property.

3. The electronic sphygmomanometer according to claim 2,
wherein the first pressure control is a depressurization control, and
wherein the heart rate is calculated based on the cuff pressure signal during pressurization control before transition to the depressurization control.

4. The electronic sphygmomanometer according to claim 1, wherein when the pressure in cuff has the same pressure value, the first pressure control unit makes the first pressure control in stages in order to measure an amplitude value of the cuff pressure signal at times when the volume change is caused and is not caused.

5. The electronic sphygmomanometer according to claim 1, wherein the causing processing unit causes the volume change at a segment from a maximum point of the cuff pressure signal to next rising point.

6. The electronic sphygmomanometer according to claim 1, wherein the cuff includes a fluid bladder for blood pressure measurement, and a blood flow blocking unit arranged on an upper-stream side with respect to the fluid bladder, the electronic sphygmomanometer further comprising:
a second pressure control unit that makes a second pressure control in order to change the pressure in the cuff to a direction opposite to the specified direction; and
a blood flow blocking unit that blocks a blood flow of the measurement site using the blood flow blocking unit only for the period of the first pressure control,
wherein the causing processing unit causes the volume change sequentially during the period of the first pressure control, and
wherein the measurement control unit comprises:
a first measurement processing unit that measures the pressure change property based on the cuff pressure signal output during the period of the first pressure control, and
a second measurement processing unit that measures the pulse wave amplitude based on the cuff pressure signal output during the period of the second pressure control.

7. The electronic sphygmomanometer according to claim 1, wherein the causing unit includes a cylinder and a drive unit for driving the cylinder.

* * * * *